United States Patent [19]

Young

[11] Patent Number: 4,847,087

[45] Date of Patent: Jul. 11, 1989

[54] SELENIUM-SULFUR COMPOSITIONS AND USES THEREFOR

[75] Inventor: Donald C. Young, Fullerton, Calif.

[73] Assignee: Union Oil Company of California, Los Angeles, Calif.

[21] Appl. No.: 858,053

[22] Filed: Apr. 30, 1986

[51] Int. Cl.$^4$ ............................................. A61K 33/04
[52] U.S. Cl. .......................................... 424/702; 71/31
[58] Field of Search .............................. 71/31; 424/162

[56] References Cited

U.S. PATENT DOCUMENTS

| | | | |
|---|---|---|---|
| 3,186,826 | 6/1965 | de Rendon | 71/6 |
| 3,295,950 | 1/1967 | Blouin et al. | 71/64 |
| 3,334,159 | 8/1967 | Campbell | 264/13 |
| 3,342,577 | 9/1967 | Blouin et al. | 71/3 |
| 3,637,351 | 1/1972 | Young et al. | 23/224 |
| 3,661,530 | 5/1972 | Block | 23/224 |
| 4,024,210 | 5/1977 | Chalmers | 264/11 |
| 4,026,694 | 5/1977 | Cross et al. | 71/11 |
| 4,133,668 | 1/1979 | Young | 71/11 |
| 4,302,237 | 11/1981 | Young | 71/11 |
| 4,388,303 | 1/1983 | Allan | 424/162 |

OTHER PUBLICATIONS

"Sulfur Oxidation" set forth in *Agrichemical Age*, Jun. 1977.

*Primary Examiner*—Frederick E. Waddell
*Attorney, Agent, or Firm*—Gregory F. Wirzbicki

[57] ABSTRACT

Ruminants such as cattle are protected against selenium-deficient diseases by applying a sulfur-selenium composition to the rangelands or pasturelands where the cattle graze. The composition preferably contains the selenium in a solid solution in the sulfur.

37 Claims, No Drawings

SELENIUM-SULFUR COMPOSITIONS AND USES THEREFOR

BACKGROUND

This invention pertains to providing nutritive supplements to mammals, in particular ruminants such as cattle.

Selenium, a nonmetallic element obtainable as a by-product in copper refining, is a required nutrient for animals. While plants do not require selenium, they will take up soluble selenates if they are present. Herbivores generally receive the required amount of nutrient selenium if there is adequate selenium in the soils where the forage plants are grown.

However, there are areas where selenium is deficient in the soil. For example, selenium is deficient in soils of California north of Colusa, most of Oregon, Wash., and southwestern Canada. There are also large areas of selenium deficiency in the northeastern United States as well as other parts of the world.

Animals, particularly ruminants, feeding in these areas frequently develop acute selenium deficiency. Acute selenium deficiency results in fetal abortion, stillbirths, and "white muscle disease" in which muscle tissues fail to develop normally. Currently, the economic loss of domestic animals in California alone from selenium deficiency is about five million dollars per year.

The present method for combating selenium deficiency in domestic animals is by veterinary therapeutic injections. It may seem an easier and more economical method to apply selenium to pasture lands and the like and thus make up for the lack of selenium in the soil, but this has not proven possible. One major reason for this is that selenates ($SeO_4{-2}$) are very toxic to man and animal and thus dangerous to handle. Moreover, the range between the minimum required level of selenium in the diet (~40 ppb) and the toxic level (approximately 20 ppm) is very narrow, and because selenates are water-soluble, two problems arise. First, if applied to the soil in amounts which are nontoxic and beneficial to cattle, the solubility of the selenates is such that any significant irrigation or rainfall will leach the selenates from the applied soil, thus leaving the soil once again in a selenium-deficient condition. On the other hand, if the selenates are applied in large amounts to ensure sufficient selenates in the soil despite rainfall, the toxicity factor becomes of concern. Specifically, if the cattle were to ingest an overdose of selenium, blindness and/or brain damage, and even death, may result.

SUMMARY OF THE INVENTION

The present invention provides a non-toxic composition of sulfur and selenium in which the selenium is contained in a water-insoluble form. Such compositions may be prepared by dissolving elemental selenium into molten, elemental sulfur, and after cooling, a solid solution is formed suitable for distribution on selenium-deficient soils. Because the selenium is not only entrapped in the sulfur, but actually dissolved therein, and because the release of selenium as a selenate is controlled by the rate at which soil bacteria consume the sulfur, the selenates are introduced into the soil at a gradual rate. In turn, the plant life upon which ruminants graze are able to take up the selenates at a correspondingly gradual rate over a relatively long period of time.

DETAILED DESCRIPTION OF THE INVENTION

This invention is directed to providing nutritional amounts of selenium to herbivores, and particularly ruminants such as cattle, by dissolving the selenium in sulfur and then applying the sulfur to the pastureland upon which the cattle graze. Although it is well known that various micronutrients can be introduced into the soil using sulfur as a carrier, the invention is unique in that, whereas the prior art sought to provide a nutrient for the plants themselves, the invention relies upon the fact that the plants, while not needing the selenium, will nevertheless take it up in sufficient amounts to prevent "white muscle disease" and other selenium-deficient ailments in cattle while avoiding a toxic excess causing other diseases or death. In addition, the invention provides the further advantages of introducing sulfur to the soil, which is of major benefit for alkaline soils, and converting the selenium to selenates in a gradual manner, thus avoiding harmful excesses of selenates while also providing a long-lasting plant and animal supplement.

The solid solutions of sulfur and selenium useful in the invention are generally made by liquifying sulfur, as by heating to its melting point, 260° F., and then dissolving elemental selenium therein. Subsequently, the melted solution is cooled, preferably into a particulate form, and the sulfur-selenium solid solution recovered. For purposes of the invention, the concentration of selenium present in the final product is typically greater than about 0.1 weight percent, usually between about 0.1 and about 4 weight percent, and preferably between about 0.5 and about 1.0 weight percent.

In the preferred embodiment, the selenium-sulfur solid solution is prepared in a highly porous form, as opposed to the dense form in which sulfur particles are typically prepared. The most highly preferred form is similar to that of Popcorn ® Sulfur, a macroparticle formed by quenching sulfur under conditions of high shear, for example, by combining a molten sulfur stream and a second fluid stream, typically a water stream, so that the net flow rate of the resultant mixture is above about 20 feet per second, preferably above 80 feet per second. Typically, the Popcorn ® Sulfur macroparticles are formed by cooling molten sulfur droplets with a fast moving stream of cool water in a vapor space. These particles have a high pore volume, for example, between about 0.06 and 0.20 cubic centimeters per gram, and a correspondingly high surface area, for example, between about 0.1 and 2.0 m²/gm. The preferred method and apparatus for producing Popcorn$^R$ Sulfur, as well as more details of the sulfur composition, are fully disclosed in three patents issued to the present inventor and Bruce A. Harbolt, U.S. Pat. Nos. 3,637,351, 3,769,378, and 3,830,631, all three of which are herein incorporated by reference in their entireties. This method, briefly, comprises injecting a molten sulfur composition into the vena contracta of a discharging orifice carrying a high velocity cooling water stream. The discharging end of the orifice is directly vented to a vapor space such as the atmosphere so as to allow the sulfur to cool while suspended in a gaseous medium. Generally, the water velocity is maintained within the range of 10 to 90 feet per second while the mass flow rate of sulfur is maintained from about 5 to 150 parts of sulfur per 100 parts of water. By forming the particles of sulfur by this method, a highly porous solid particle can be obtained, which particle is especially useful as a soil supplement. In the present invention, of course, the foregoing procedure, and the procedure taught in the three above-identified patents, is modified to the extent that, instead of using molten sulfur, a molten sulfur-selenium solution is used, which may optionally contain added plant micronutrients and/or hydrocarbons for heterotropic bacteria, as described in fuller detail hereinafter.

When prepared in the form of a Popcorn® Sulfur analog, the selenium-sulfur compositions of the invention are highly porous, having a pore volume above about 0.04 cc/gm, typically in the range of 0.04 to 0.20 cc/gm., and generally about 0.05 to 0.15 cc/gm., as measured by the modified Wheeler test described in the above-identified three patents. In addition, the sulfur-selenium particulate compositions of this embodiment of the invention have a bulk density in the range of 0.9 to 1.4 gm/cc, e.g., 0.90 to 1.3 gm/cc, and oftentimes in the range of 0.97 to 1.11 gm/cc., e.g., from 1.05 to 1.09. Further still, these compositions have an average particle diameter from about 0.02 to 0.11 inch, a maximum angle of repose between about 30° and 40°, and a high surface area. The surface areas reported in the above-identified patents were estimated values based on calculation, i.e., from 0.06 to 0.09 m/gm; however, when subsequently tested by a nitrogen adsorption BET method, the surface areas were found to be surprisingly—and fortunately—far higher, on the order of 0.1 to 5.0 $m^2/gm$, usually from 0.1 to 2.0 $m^2/gm$.

Particulate sulfur distributed upon a soil is made available to plant life by oxidation, and being an element essential to plant life, the present invention offers the dual advantages of promoting plant growth as well as overcoming selenium-deficiency of ruminant animals. In addition, for alkaline soils, sulfur also acts as a soil amendment, to increase the water intake and aeration of the soil, improve the physical conditions of the soil, eliminate or ameliorate the harmful effects of alkalinity and sodium problems of the soil, and increase the availability of certain nutrients and elements necessary for plant growth and life. Thus, it can be seen that maximum advantage is obtained in the invention when the soil upon which the sulfur-selenium composition of the invention is distributed is not only selenium deficient but also sulfur deficient and/or highly alkaline. Such soils are commonplace in many western regions of the United States, as well as all arid and semi-arid regions of the world.

Although the invention is not to be held to any particular theory of operation, it is well known that sulfur introduced into soils is oxidized by bacteria of the Thiobaccilus genus, yielding sulfur in a form (i.e., sulfate) more desirable for plant life. This oxidation method improves soil conditions and is well known to be relatively slow, at least in comparison to directly introducing sulfates into the soil, as by applying calcium sulfate, ammonium sulfate, and the like to the soil. (For example, sulfur conversions to sulfate typically have a relatively long half life of about 6 months in agricultural soils.) But in the invention, this slow rate of release works to advantage, because the dissolved selenium is also oxidized at a slow rate, releasing selenates gradually to the soil at fairly uniform rates over a relatively long period of time. In this manner, the selenates in the soil are not only prevented from reaching toxic levels but, to the contrary, are maintained at levels beneficial to the ruminant animals.

Generally speaking, when the selenium-sulfur compositions are prepared to contain selenium in the concentration range of 0.1 to 5.0 weight percent, there will be no difficulty encountered in exceeding toxic levels, assuming, of course, that the oxidation of the sulfur-selenium composition is allowed to proceed normally by oxidation as described. Nevertheless, it should be understood that the rate of oxidation, and thus the release of selenates to the soil in a form the plant can take up, is dependent upon a number of factors including:

(1) Total Distribution. Typically, the sulfur-selenium particulate composition in the invention is distributed upon the soil so as to provide about 50 to 2,000 pounds per acre, preferably 50 to 500 pounds per acre, of said composition. Clearly, for a given soil and a given concentration of selenium in the composition, the more particles distributed, the faster the release of selenates into the soil.

(2) Selenium Concentration. The greater the selenium concentration, the faster the release of selenates to a given soil. To prevent introducing toxic levels of selenates from being released to the soil, a safe maximum concentration is about 5.0 weight percent when the distribution rate is as set forth in paragraph (1) above.

(3) Surface Area. The higher the surface area of a sulfur particle, the greater the opportunity for the Thiobacillus bacteria to feed. Thus, increasing the surface area of the particle has the effect of increasing the rate at which both the sulfur and selenium are oxidized and introduced into the soil. High surface areas, when desired, may be obtained either by grinding or, more preferably, by preparing the sulfur in a form analogous to Popcorn® Sulfur.

(4) Particle Size and Porosity. Generally speaking, increasing porosity and/or decreasing particle size tends to increase the rate at which selenium is converted into selenates and taken up by the plant. This will be illustrated more fully in Example III hereinafter.

(5) Hydrocarbon Additives. It has been disclosed above that various plant nutrients can be added to the compositions of the invention, for example, nutrients containing boron, copper, zinc, iron, magnesium, manganese, and molybdenum. However, one may also add any of a number of paraffinic based hydrocarbons to the present compositions, in a manner similar to that disclosed in my U.S. Pat. No. 4,133,668, herein incorporated by reference in its entirety. Such hydrocarbons not only aid in uniformly distributing the plant nutrients throughout the sulfur-selenium composition, but even in the absence of such nutrients there is an advantage. Specifically, some members of the Thiobaccilus family, and more specifically still, the heterotropic members, feed on either sulfur or paraffinic hydrocarbons as opposed to only on sulfur as is the case with the homotropic members. Thus, by adding a paraffinic hydrocarbon to the compositions herein, the rate at which the selenates are introduced into the soil is increased, as the composition is made more attractive to more of the bacteria which can oxidize the sulfur and selenium to sulfates and selenates, respectively.

(6) Soil Conditions. As described in the article "Sulfur Oxidation," Agrichemical Age, June, 1977, E. Hugh Gardner and Robert Costa reported that the oxidation of elemental sulfur in soils is dependent upon soil conditions such as pH, temperature, aeration, moisture, and the microbial population. However, it is generally the case that the soil conditions do not have to be altered significantly, and this because the rate of selenium conversion to selenates tends to increase when plant life is most active and decrease when plant life is dormant or encountering adverse conditions. The reason for this is that the release rate of selenates is dependent upon bacteria, which, being closely related biologically to plant organisms, tend to thrive under conditions most stimulating for plants and to lessen their activity when conditions for plant growth are adverse. This fact works to advantage in the invention since, for any given application of the sulfur-selenium composition to the soil, selenates are not underproduced when plant life is most active or overproduced when plant life is dormant or facing adverse circumstances. The net effect is that the plant life—regardless of soil conditions—tends to take up selenates at a rate providing in the plants a relatively constant concentration of selenium, or at least a concentration varying within more narrow ranges than one would otherwise expect. In turn, the cattle and other ruminants feeding on the plant life ingest selenium at either a constant rate or a rate varying within a relatively narrow range.

Many of the advantages of the present invention have been explained above, but one which should be stressed is that the invention provides, surprisingly, for a solid solution of selenium and sulfur. This solution has been found to be totally innocuous to ruminants, should they ingest it, because the selenium is not in the form of poisonous selenates. In addition, since a solution is the ultimate form of a dispersion, it can be seen that, in the preferred embodiment wherein the sulfur and selenium are thoroughly blended to a homogeneous composition, the resulting solid solution will contain no "pockets" high in selenium concentration. Therefore, the oxidation to selenates will proceed gradually, although not necessarily at a perfectly constant rate.

In addition still, the solid solutions of the invention provide the advantage of rendering the selenium water-insoluble until the Thiobaccilus bacteria oxidize the selenium to selenates. It is one of the discoveries of the invention that the Thiobaccilus bacteria attack sulfur and selenium indiscriminately and apparently do not distinguish the two elements. Thus, the invention provides a water-insoluble, nontoxic selenium component for the soil, which only gradually releases water-soluble selenates. Thus, a major rainfall will have little or no impact upon the effectiveness of selenium distributed on the soil because only those selenates which have been released and not yet taken up by the plant life will be affected by rainfall.

Because the sulfur-selenium compositions of the invention are essentially immune to rainfall and other water conditions, and because the selenium is only released gradually to the soil, the invention provides selenium to the plant life and thence to the ruminants over a long period of time. At present, it is believed that a five to six-year supply of selenium, adequate for ruminant dietary levels, can be obtained by distributing upon the soil between about 50 and 500 pounds per acre of sulfur-selenium compositions, having concentrations of selenium between about 0.1 to 4.0 weight percent. Of course, the exact amounts and concentrations for a given application will depend on many of the factors hereinbefore enumerated, and results may prove variable from soil to soil. Nevertheless, in most cases, the foregoing ranges of distribution levels and selenium concentrations will generally assure protection for ruminants against diseases caused by selenium-deficient soils.

The following Examples are provided to illustrate various aspects of the invention, and as such, the Examples are for illustrative purposes only. The Examples are not meant to limit the invention, the scope of which is defined in the claims.

EXAMPLE I

A laboratory apparatus for making prilled sulfur was comprised of a 10-liter stainless steel heating vessel, equipped with a heating element to heat the contents to the melting point of sulfur, the vessel being insulated and closed at the top for efficiency purposes. At a lower elevation was a second vessel containing about 5 gallons of water at ambient temperature. Both the first and second vessels were equipped with stirrers, powered by air-driven motors, and the second vessel contained a baffle to prevent vortexing and to increase shear. Between the first and second vessels was a pipe, maintained at about 300° F. by suitable heating means, with a valve to control the gravity flow of molten material from the first vessel to the second.

In operation, elemental sulfur and powdered elemental selenium were added to the first vessel in a total weight amount of about 5 pounds. The mixture was then heated and stirred to assure a uniform blend, and, upon inspection, it was seen that the selenium readily dissolved in the molten sulfur. The molten sulfur-selenium solution was then passed to the second vessel, and, upon contact with the stirred water, a prilled material was formed.

In the experiment, three different materials of the following nominal analyses were made: 0.25 weight percent, 1.0 weight percent, and 4.0 weight percent selenium. Upon analysis of each material, it was found that the actual percentages were: 0.25 weight percent, 0.92 weight percent, and 3.90 weight percent, respectively.

One thousand grams of each of the three materials was then passed through a series of screens and the weight percentages which remained on the screens is shown in the following table:

TABLE I

| U.S. Standard Mesh # | Mesh Openings in mm. | % Retained Nominal Selenium Concentration | | |
|---|---|---|---|---|
| | | 0.25% | 1.00% | 4.00% |
| 6 | 3.36 | 4.85 | 1.05 | 15.92 |
| 8 | 2.38 | 34.25 | 22.08 | 34.73 |
| 10 | 2.00 | 15.80 | 14.28 | 12.36 |
| 12 | 1.68 | 10.32 | 11.53 | 7.38 |
| 14 | 1.41 | 9.00 | 11.48 | 6.44 |
| 16 | 1.19 | 5.62 | 8.23 | 4.02 |
| 18 | 1.00 | 3.80 | 6.02 | 2.89 |
| 20 | 0.841 | 4.19 | 7.08 | 3.65 |
| 40 | 0.420 | 8.10 | 12.73 | 8.53 |
| 50 | 0.297 | 2.33 | 2.71 | 2.45 |
| 100 | 0.149 | 1.33 | 1.69 | 1.17 |
| 200 | 0.074 | 0.41 | 0.77 | 0.36 |
| <200 | <0.074 | 0.07 | 0.21 | 0.04 |

EXAMPLE II

Quench water used to make the three prilled materials of Example I was analyzed for selenium content and found in each instance to contain less than 2 milligrams per liter of selenium (the limit of detection). It was therefore concluded that the sulfur-selenium solution does not contain selenium in a water-soluble form. (By "water-soluble," it is meant that, when introduced into water at ambient conditions, no more than about 1 percent of the selenium in the composition will dissolve into the water.)

EXAMPLE III

Samples of the 4% selenium-sulfur compositions prepared in Example I, having a relatively high porosity, were screened into 14 size fractions ranging from 4 to 200 mesh. Also screened into the same fractions were nonporous 4% selenium-sulfur compositions prepared by casting molten 4% selenium-sulfur solutions in 2 in.×4 in.×1 in. aluminum pans, which solutions, after cooling, were crushed and screened to the designated fractions.

Agricultural soil (Delano Sandy Loam) was screened through a 10-mesh screen. The soil was then placed in enough 6-inch pots (about 2,000 grams per pot) to test each of the 28 fractions above described, plus a control. The sulfur-selenium compositions were then added to twenty-eight of the pots at a rate of 6,000 pounds per acre of 6-inch soil. Since an acre-6-inch soil weighs about 2 million pounds, about 6 grams of the sulfur-selenium composition was added per pot, by thorough mixing with the loam. Each mesh size type of sulfur-selenium composition was tested in a separate experiment, and each experiment was then replicated four times. In the tests, eight Milo seeds were planted in each of the 116 pots, which were then maintained in the greenhouse for three months. During the Milo growth period, the pots were watered as required, and a complete nutrient solution applied to maintain vigorous growth. At the end of the test period, the Milo plants in each pot were harvested, dried, and analyzed for selenium content. The results are shown in Table II.

TABLE II

| Mesh Size | Porous Sulfur, Se in Plants, wppm* | Nonporous Sulfur, Se in Plants, wppm* |
|---|---|---|
| 4 | 180 | 110 |
| 6 | 290 | 195 |
| 8 | 295 | 170 |
| 10 | 290 | 190 |
| 12 | 320 | 190 |
| 14 | 600 | 215 |
| 16 | 610 | 305 |
| 18 | 620 | 345 |
| 20 | 625 | 440 |
| 50 | 720 | 450 |
| 80 | 1220 | 470 |
| 100 | 1710 | 500 |
| 200 | 1440 | 520 |
| <200 | 2490 | 600 |

*Mean of 4 replicates

The data in Table II establish at least three facts. First, because the control plants only took up to 5 wppm selenium from the soil itself, the selenium concentration of plants can be significantly increased regardless of which composition is applied to the soil. Second, it is clear that the porous sulfur-selenium composition is more effective for faster selenium uptake than the nonporous sulfur-selenium composition. And third, the selenium uptake rate is a function of the particle size and porosity (other things being equal), so that, by adjusting these two parameters plus the concentration of selenium in the sulfur-selenium solution and the total amount applied to the soil, one can control the selenium uptake rate or the plant life.

It will, of course, require some experimentation in any individual case to determine the optimum adjustment of these various parameters. Moreover, the rates demonstrated in Example III are not necessarily those which should be used in commercial practice. The experiment of Example III was designed not only to show that selenium can be introduced into plant life by the method of the invention but also to enhance the difference in uptake rates between porous and nonporous sulfur-selenium compositions. Nevertheless, many of the values shown in Table II are within tolerable dietary limits when it is considered that plant weight is about 95% water and the values in Table II are on a dry basis. When appropriately corrected (by multiplying by 0.05), it will be seen that many of the values in Table II fall within the dietary range of 40 ppb to 20 ppm selenium. However, since many values are outside this dietary range, it is recommended in actual practice that significantly less of the selenium-sulfur composition be used per acre than was the case in this experiment.

Although the invention has been described in conjunction with examples and preferred embodiments, it is evident that the invention is capable of many alternatives, modifications, and variations. Accordingly, it is intended to embrace within the invention all such alternatives, modifications, and variation that fall within the spirit and scope of the appended claims.

I claim:

1. A composition comprising a solid solution comprising elemental selenium and elemental sulfur, said selenium being present in said solution in a concentration greater than about 0.1 weight percent.

2. A composition as defined in claim 1 in particulate form.

3. A composition as defined in claim 2 having a pore volume greater than 0.04 cc./gm.

4. A composition as defined in claim 3 having a surface area greater than 0.1 m²/gm.

5. A composition as defined in claim 4 having a pore volume between about 0.04 and 0.20 cc./gm.

6. A composition as defined in claim 5 having a bulk density from 0.90 to 1.3 gm./cc.

7. A composition as defined in claim 6 having an average particle diameter from about 0.02 to 0.11 inch.

8. A composition as defined in claim 5 having an average particle diameter from about 0.02 to 0.11 inch.

9. A composition as defined in claim 1 wherein the concentration of selenium is between about 0.1 and about 5.0 weight percent.

10. A composition as defined in claim 8 wherein the concentration of selenium is between about 0.1 and about 4.0 weight percent.

11. A composition as defined in claim 5 wherein the concentration of selenium is between about 0.5 and about 1.0 weight percent.

12. A composition as defined in claim 2 wherein the concentration of selenium in said solid solution is between about 0.1 and about 4.0 weight percent.

13. A composition as defined in claim 7 wherein the concentration of selenium in said solid solution is between about 0.1 and about 5.0 weight percent.

14. A composition comprising a solid solution comprising elemental selenium and elemental sulfur, said selenium being present in said solution in a concentration effective for increasing the selenium content of plants growing in selenium-deficient soils.

15. A particulate composition comprising elemental selenium dissolved in elemental sulfur in a concentration effective for increasing the selenium content of plants growing in selenium-deficient soils.

16. A composition as defined in claim 15 having a pore volume between about 0.04 and 0.20 cc./gm.

17. A composition as defined in claim 16 having a bulk density from 0.90 to 1.3 gm./cc.

18. A composition as defined in claim 17 having an average particle diameter from about 0.02 to 0.11 inch.

19. A composition as defined in claim 18 having a surface area from about 0.1 to about 5.0 $m^2$/gm.

20. A composition as defined in claim 19 wherein the concentration of selenium is between about 0.1 and about 4.0 weight percent.

21. A composition as defined in claim 2 further comprising one or more plant micronutrients.

22. A composition as defined in claim 8 further comprising one or more plant micronutrients.

23. A composition as defined in claim 20 further comprising one or more plant micronutrients.

24. A composition as defined in claim 7 further comprising one or more plant micronutrients.

25. A composition consisting essentially of a solid solution of elemental selenium and elemental sulfur, the selenium being contained in said solution in a concentration greater than about 0.1 weight percent.

26. A composition as defined in claim 25 in particulate form.

27. A composition as defined in claim 26 having a pore volume between about 0.04 and 0.20 cc./gm.

28. A composition as defined in claim 26 having a pore volume between about 0.04 and 0.15 cc./gm., and a surface area from about 0.1 to about 2.0 $m^2$/gm.

29. A composition as defined in claim 28 having an average particle diameter from about 0.02 to 0.11 inch.

30. A composition as defined in claim 29 wherein the concentration of selenium is between about 0.1 and about 5.0 weight percent.

31. A composition comprising the product produced by dissolving elemental selenium into liquid elemental sulfur and then solidifying the resulting admixture, said admixture containing greater than about 0.1 weight percent of selenium.

32. A composition as defined in claim 31 wherein the composition is in particulate form.

33. A composition as defined in claim 32 wherein the composition has a pore volume greater than 0.04 cc/gm, a surface area greater than 0.1 $m^2$/gm, a pore volume between 0.04 and 0.20 cc/gm, a bulk density from 0.90 to 1.3 gm/cc, and an average particle diameter from about 0.02 to 0.11 inch.

34. A composition as defined in claim 32 wherein the concentration of selenium is between about 0.1 and 5.0 weight percent.

35. A composition as defined in claim 33 wherein the concentration of selenium is between about 0.1 and 5.0 weight percent.

36. A composition consisting essentially of a solid solution of elemental selenium and elemental sulfur, the selenium being contained in said solution in a concentration effective for increasing the selenium content of plants growing in selenium-deficient soils.

37. A composition comprising the product produced by dissolving elemental selenium into liquid elemental sulfur and then solidifying the resulting admixture, said admixture containing the elemental selenium in a concentration effective for increasing the selenium content of plants growing in selenium-deficient soils.

* * * * *